United States Patent [19]

Arthur, III

[11] Patent Number: 4,978,335
[45] Date of Patent: Dec. 18, 1990

[54] INFUSION PUMP WITH BAR CODE INPUT TO COMPUTER

[75] Inventor: William D. Arthur, III, Apharetta, Ga.

[73] Assignee: Medex, Inc., Hilliard, Ohio

[21] Appl. No.: 414,371

[22] Filed: Sep. 29, 1989

[51] Int. Cl.$^5$ .............................................. A61M 5/20
[52] U.S. Cl. ..................................... 604/67; 604/155; 128/DIG. 1; 235/375
[58] Field of Search ................... 604/65, 67, 151, 152, 604/154, 155; 128/DIG. 12, DIG. 1; 235/375

[56] References Cited

U.S. PATENT DOCUMENTS

| | | | |
|---|---|---|---|
| 4,573,994 | 3/1986 | Fischell et al. | 604/891 |
| 4,624,658 | 11/1986 | Mardorf et al. | 604/154 X |
| 4,652,260 | 3/1987 | Fenton, Jr. et al. | 604/67 |
| 4,767,406 | 8/1988 | Wadham et al. | 604/67 X |
| 4,838,857 | 6/1989 | Strowe et al. | 604/65 X |
| 4,853,521 | 8/1989 | Claeys et al. | 604/407 X |

Primary Examiner—C. Fred Rosenbaum
Assistant Examiner—Corrine Maglione
Attorney, Agent, or Firm—Wood, Herron & Evans

[57] ABSTRACT

An infusion pump has a housing for receipt of a syringe, a motor to drive the plunger of the syringe to expel a medicant within the syringe, a computer for controlling the motor and a place to mount the syringe. A bar code reader is mounted adjacent the syringe and the syringe has a pharmacist-applied bar code that programs the computer with the data for the dispensing of the medicant.

2 Claims, 1 Drawing Sheet

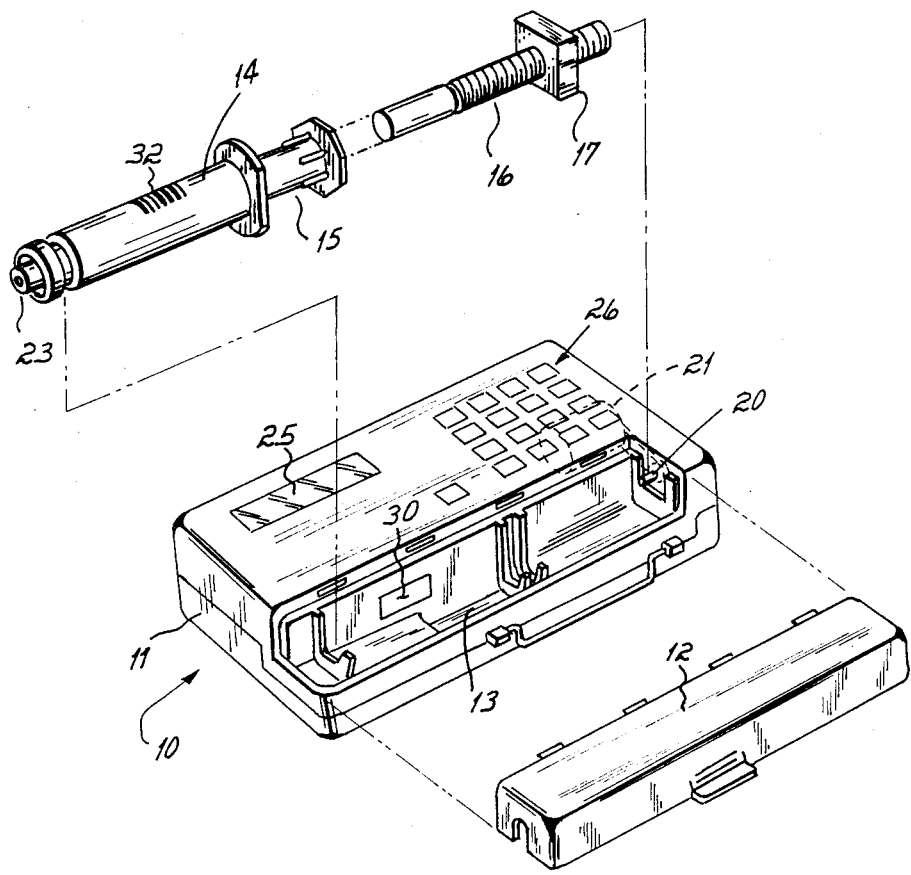

INFUSION PUMP WITH BAR CODE INPUT TO COMPUTER

BACKGROUND OF THE INVENTION

This invention relates to an infusion pump of the type described in U.S. Pat. No. 4,529,401, that is, an infusion pump having a computer to control the dispensing of the medicant.

More specifically, the infusion pump of the '401 patent has a housing and a replaceable syringe mounted in the housing. A motor, mounted in the housing, is connected to the syringe plunger to drive the plunger axially in order to expel the medicant within the syringe into a patient. A computer is connected to the motor and a keyboard associated with the computer is provided for entering data concerning the dispensing of the medicant, the data including concentration, delivery modes and dosage data including the basal rate.

It is contemplated that the computer keyboard be patient-operated so that the infusion pump is of general application. The computer is thus modifiable for each patient's requirements through the manipulation of the keyboard. But, some patients cannot cope with the keyboard or should not be permitted to cope with the keyboard. The possibility of patient injury through improper operation of the keyboard is present.

Another form of infusion pump has been proposed. In that form, critical information can be inputted into the computer only by an authorized person such as a pharmacist. For that purpose, a secret code is required for the complete operation of the keyboard. But, that form of infusion pump has its disadvantages, the principal one being that the programmed infusion pump must be dedicated to a particular patient.

BRIEF SUMMARY OF THE INVENTION

It is an objective of the present invention to provide an infusion pump which is of universal application as to patient and medicant, but which prevents injury to the patient through inadvertent operation.

This objective of the invention is obtained by providing, in the infusion pump, a bar code reader or means to automatically enter a bar code instruction to input to the pump computer data which has heretofore been inputted by keyboard. The syringe has a bar code mounted on it so that the medicant within is that provided by the pharmacist in accordance with the prescription for the medicine. The pharmacist, given the prescription, prepares the syringe with the patient-tailored bar code on it.

In use, the physician prepares the prescription for the medicine and this is given to the pharmacist. The prescription is filled and placed in one or more syringes. A bar code having the prescription data on it is prepared and, in label form, is mounted or attached to the syringe. The operator inserts the syringe into the pump housing. The bar code reader reads the bar code when the syringe is inserted in the housing and inputs the prescribed data to the pump computer. The infusion pump is thus programmed to be operated only in accordance with the physician-prepared prescription.

It is of course contemplated that some operator modification of the dispensing of the medicant will be permitted as, for example, the introduction of a supplemental dose or a bolus, but the bar code data would limit the amounts, frequency and so forth, so that while the patient could modify his intake of the medicant, the patient could not injure himself in the process because of the limits put on the patient operation by the bar code.

The several features of the invention will become more readily apparent from the following detailed description taken in conjunction with the accompanying drawings in which:

The FIGURE is a disassembled perspective view of the invention.

It is contemplated that the present invention is an improvement in known infusion pumps, and an example of the type of pump to which the invention is directed is found in U.S. Pat. No. 4,529,401. A description is completely incorporated herein by reference.

DETAILED DESCRIPTION OF THE DRAWINGS

The pump is indicated at 10 in the drawing and includes a housing having a closure cap 12. The housing provides a chamber 13 for receipt of a syringe 14. The syringe has a plunger 15. A screw 16 is mounted within the plunger and has a nut 17.

When the syringe is mounted in the housing 11, the nut is fixed by the walls of the chamber 13 against rotation. The screw is connected to a drive pin 20 connected to a motor 21 shown in phantom lines. Operation of the motor causes the screw to rotate with respect to the nut 17. Since the nut is fixed the screw moves axially, driving the plunger toward the dispensing end 23 of the syringe to expel the medicant from within the syringe.

The housing has a computer which preferably includes a display 25 for display of such data as the patient needs for his observation. A keyboard 26 is provided for the introduction of the limited amount of data into the computer to permit certain operations which the patient is permitted to control.

A bar code reader 30 is mounted in or easily connected to the pump in the housing and is connected to the computer to input data from a bar code to the computer. A bar code 32 is mounted on the face of the syringe. Preferably, the bar code is in a label form that is prepared by the pharmacist and mounted by the pharmacist on the syringe so as to program the computer for the specific medicant that is in the syringe and for the specific patient for whom the medicant is prescribed. The bar code is adapted to be read by the bar code reader when the syringe is inserted into the chamber 13. The bar code could be interrogated before, during, or after syringe mounting. When the syringe is inserted in the chamber 13, the cap 12 is applied to enclose the syringe within the chamber.

In operation, the patient obtains a prescription for the medicant from his physician. The patient takes the prescription to the pharmacist. The pharmacist fills one or more syringes of a size to fit the housing 11 with the medicant prescribed. The pharmacist enters in a machine known in the art the necessary data concerning the medicant and its concentration, dosage and so forth. That data is printed by the machine in bar code form on labels which the pharmacist mounts in a designated place on the syringe.

The operator places a syringe having the bar code data on it in the housing with the bar code adjacent the bar code reader. The bar code reader reads the data and inputs the data to the computer. Thereupon, the infusion pump is ready for the administration of the prescribed dosage to the patient while permitting the operator to make permitted alterations in the mode and dosage.

While the invention has been described with specific reference to a bar code and reader, it is to be understood that the invention is also applicable to other machine-readable indicia such as magnetic strips, user insertable memory keys or tags, etc.

Having thusly described my invention, I claim:

1. An infusion pump comprising:
   a housing,
   mounting means on said housing for a syringe having a plunger,
   means including a motor connected to said plunger for driving said plunger at a preselected rate,
   a computer connected to said motor for controlling the operation of said plunger,
   said computer being capable of receiving data relating to a patient's dosage requirements and converting that data to an output that controls said motor to drive said plunger in accordance with received data,
   a reader for machine-readable computer data connected to said computer,
   a syringe having a plunger and having machine-readable data mounted on the syringe and containing data relating to a patient's dosage requirement,
   said reader, upon reading said data, controlling the operation of said motor and hence the dispensing of medicant in said syringe, said syringe being mounted by said mounting means to enable said reader to read said data and program said computer for a particular patient's requirements.

2. Apparatus as in claim 1 in which said reader is a bar code reader and said data being in the form of a bar code on said syringe.

* * * * *